United States Patent
Samsodin et al.

(10) Patent No.: US 9,885,006 B2
(45) Date of Patent: Feb. 6, 2018

(54) PREPARATION OF BIOPOLYOL ESTERS FOR LUBRICANT APPLICATION

(71) Applicant: PETROLIAM NASIONAL BERHAD, Kuala Lumpur (MY)

(72) Inventors: Normawati Samsodin, Kuala Lumpur (MY); Sara Shahruddin, Kuala Lumpur (MY); Farah Fazlina M Yasin, Kuala Lumpur (MY)

(73) Assignee: Petroliam Nasional Berhad, Kuala Lumpur (MY)

( * ) Notice: Subject to any disclaimer, the term of this patent is extended or adjusted under 35 U.S.C. 154(b) by 0 days.

(21) Appl. No.: 14/771,137

(22) PCT Filed: Feb. 28, 2014

(86) PCT No.: PCT/MY2014/000026
§ 371 (c)(1),
(2) Date: Aug. 27, 2015

(87) PCT Pub. No.: WO2014/133380
PCT Pub. Date: Sep. 4, 2014

(65) Prior Publication Data
US 2016/0002569 A1    Jan. 7, 2016

(30) Foreign Application Priority Data
Feb. 28, 2013 (MY) .......................... PI 2013000713

(51) Int. Cl.
*C07C 59/147* (2006.01)
*C11C 3/00* (2006.01)
(Continued)

(52) U.S. Cl.
CPC .............. *C11C 3/003* (2013.01); *C07C 67/08* (2013.01); *C10M 105/42* (2013.01);
(Continued)

(58) Field of Classification Search
CPC ...... C11C 3/003; C07C 67/08; C10M 105/42; C10M 107/32
(Continued)

(56) References Cited

U.S. PATENT DOCUMENTS

| 667,043 A | 1/1901 | Steep |
| 2,401,338 A | 6/1946 | Dunmire |

(Continued)

FOREIGN PATENT DOCUMENTS

| AU | 165032 | 2/1954 |
| CN | 101077856 A | 11/2007 |

(Continued)

OTHER PUBLICATIONS

Ackman et al., "Ozonolysis of Unsaturated Fatty Acids. I. Ozonolysis of Oleic Acid," Can. J. Chem., 39:1956-1963 (1961).
(Continued)

*Primary Examiner* — Deborah D Carr
(74) *Attorney, Agent, or Firm* — LeClairRyan, a Professional Corporation

(57) ABSTRACT

Ester polyol esters are a unique class of lubricants that have adjustable molecular weights, viscosities, and pour points based on the character of their reaction materials and relative ratios. There is provided a method for preparing at least one ester polyol ester, the method comprising the method comprising preparing a reaction mixture comprising at least one polyol compound; at least one dicarboxylic acid; and at least one monocarboxylic acid, wherein the at least one polyol compound is esterified with the at least one dicarboxylic acid and the at least one monocarboxylic acid, wherein the reaction mixture has a hydroxyl group to carboxyl group ratio (HCR) corresponding to a ratio of moles of hydroxyl groups to moles of carboxyl groups, and the HCR is less than about 1.

15 Claims, 7 Drawing Sheets

TMP Trioleate

(51) Int. Cl.
*C07C 67/08* (2006.01)
*C10M 105/42* (2006.01)
*C10M 107/32* (2006.01)

(52) U.S. Cl.
CPC .... *C10M 107/32* (2013.01); *C10M 2207/301* (2013.01); *C10N 2220/022* (2013.01); *C10N 2220/023* (2013.01); *C10N 2230/06* (2013.01); *C10N 2230/10* (2013.01); *C10N 2230/64* (2013.01); *C10N 2230/66* (2013.01); *C10N 2270/00* (2013.01); *Y02P 30/20* (2015.11)

(58) Field of Classification Search
USPC .......................................................... 554/121
See application file for complete search history.

(56) References Cited

U.S. PATENT DOCUMENTS

| | | | |
|---|---|---|---|
| 2,566,559 | A | 9/1951 | Dolnick et al. |
| 2,813,113 | A | 11/1957 | Goebel et al. |
| 2,997,493 | A | 8/1961 | Huber |
| 3,048,608 | A | 8/1962 | Girard et al. |
| 4,061,581 | A | 12/1977 | Leleu et al. |
| 4,298,730 | A | 11/1981 | Galleymore et al. |
| 4,313,890 | A | 2/1982 | Chu et al. |
| 4,865,879 | A | 9/1989 | Finlay |
| 5,736,748 | A | 4/1998 | Lysenko et al. |
| 5,773,256 | A | 6/1998 | Pelenc et al. |
| 5,773,391 | A * | 6/1998 | Lawate ............... C07C 69/52 508/257 |
| 6,107,500 | A | 8/2000 | Prossel et al. |
| 6,362,368 | B1 | 3/2002 | Frische et al. |
| 7,125,950 | B2 | 10/2006 | Dwan'Isa et al. |
| 7,192,457 | B2 | 3/2007 | Murphy et al. |
| 7,241,914 | B2 | 7/2007 | Wartini et al. |
| 7,589,222 | B2 | 9/2009 | Narayan et al. |
| 9,260,372 | B2 | 2/2016 | Benecke et al. |
| 9,302,976 | B2 | 4/2016 | Benecke et al. |
| 9,505,701 | B2 | 11/2016 | Garbark et al. |
| 2004/0167343 | A1 | 8/2004 | Halpern et al. |
| 2005/0112267 | A1 | 5/2005 | Kian et al. |
| 2006/0194974 | A1 | 8/2006 | Narayan et al. |
| 2009/0216040 | A1 | 8/2009 | Benecke et al. |
| 2009/0239964 | A1 | 9/2009 | Sasaki et al. |
| 2010/0087350 | A1 | 4/2010 | Sonnenschein et al. |
| 2010/0117022 | A1 * | 5/2010 | Carr ................... C10M 105/44 252/68 |
| 2011/0077350 | A1 | 3/2011 | Malotky et al. |
| 2011/0269979 | A1 | 11/2011 | Benecke et al. |
| 2011/0269981 | A1 | 11/2011 | Benecke et al. |
| 2011/0269982 | A1 | 11/2011 | Benecke et al. |
| 2012/0184758 | A1 | 7/2012 | Krull et al. |
| 2015/0005520 | A1 | 1/2015 | Benecke et al. |
| 2015/0018260 | A1 | 1/2015 | Benecke et al. |
| 2015/0018444 | A1 | 1/2015 | Garbark et al. |
| 2015/0080599 | A1 | 3/2015 | Garbark et al. |
| 2015/0087850 | A1 | 3/2015 | Benecke et al. |

FOREIGN PATENT DOCUMENTS

| | | |
|---|---|---|
| CN | 101195577 A | 6/2008 |
| CN | 201343513 | 11/2009 |
| CN | 101812349 A | 8/2010 |
| CN | 101899160 A | 12/2010 |
| CN | 102010772 A | 4/2011 |
| EP | 0010333 A1 | 4/1980 |
| EP | 1260497 A2 | 11/2002 |
| EP | 1529828 A1 * | 5/2005 |
| EP | 1533360 A1 * | 5/2005 |
| GB | 915461 | 1/1963 |
| JP | S57185235 A | 11/1982 |
| JP | 04018049 A | 1/1992 |
| JP | 2008013546 A | 1/2008 |
| KR | 10-2008-0023290 A | 3/2008 |
| MY | 140833 A | 1/2010 |
| WO | 93/24585 A1 | 12/1993 |
| WO | WO93024585 A1 * | 12/1993 |
| WO | 98/50338 A1 | 11/1998 |
| WO | 0039068 A1 | 7/2000 |
| WO | 2004087847 A1 | 10/2004 |
| WO | 2006/093874 A2 | 9/2006 |
| WO | 2006093874 A2 | 9/2006 |
| WO | 2007027223 A2 | 3/2007 |
| WO | 2010/056449 A2 | 10/2009 |
| WO | 2010/078505 A1 | 7/2010 |
| WO | 2010/085545 A1 | 7/2010 |
| WO | 2010078491 A1 | 7/2010 |
| WO | 2010078493 A1 | 7/2010 |
| WO | 2010078498 A1 | 7/2010 |
| WO | 2010078505 A1 | 7/2010 |
| WO | WO 2010078505 A1 * | 7/2010 |
| WO | 2013129907 A1 | 9/2013 |
| WO | 2013129908 A1 | 9/2013 |
| WO | 2013129909 A1 | 9/2013 |
| WO | 2013129910 A1 | 9/2013 |
| WO | 2013129911 A1 | 9/2013 |

OTHER PUBLICATIONS

Yunus et al., "Preparation and Characterization of Trimethylolpropane Esters from Palm Kernel Oil Methyl Esters," J. Oil Palm Research, 15(2):42-49 (2003).
Spyros, A., "Quantitative Determination of the Distribution of Free Hydroxylic and Carboxylic Groups in Unsaturated Polyester and Alkyd Resins by 31 P-NMR Spectroscopy," J. Appl. Polym. Sci., 83:1635-1642 (2002).
PCT International Search Report and Written Opinion for International Patent Application No. PCT/MY2013/000038 (Jun. 27, 2013).
PCT International Search Report and Written Opinion for International Patent Application No. PCT/MY2013/000039 (Jun. 27, 2013).
PCT International Search Report and Written Opinion for International Patent Application No. PCT/MY2013/000040 (Jun. 28, 2013).
PCT International Search Report and Written Opinion for International Patent Application No. PCT/MY2013/000041 (Jun. 28, 2013).
PCT International Search Report and Written Opinion for International Patent Application No. PCT/MY2013/000042 (Jun. 28, 2013).
International Preliminary Report on Patentability for International Patent Application No. PCT/MY2013/000038 (Sep. 12, 2014).
International Preliminary Report on Patentability for International Patent Application No. PCT/MY2013/000039 (Sep. 12, 2014).
International Preliminary Report on Patentability for International Patent Application No. PCT/MY2013/000040 (Sep. 12, 2014).
International Preliminary Report on Patentability for International Patent Application No. PCT/MY2013/000041 (Sep. 12, 2014).
International Preliminary Report on Patentability for International Patent Application No. PCT/MY2013/000042 (Sep. 12, 2014).
Third Party Submission for U.S. Appl. No. 14/381,554 dated Jul. 13, 2015.
Extended European Search Report for EP13755362.4 dated Aug. 21, 2015.
Extended European Search Report for EP13754711.3 dated Sep. 3, 2015.
PCT International Search Report and Written Opinion corresponding to PCT/MY2014/000026, filed Feb. 28, 2014 (mailed May 21, 2014).
Office Action for China Application No. 201380022561.5 (Apr. 18, 2016).
Sebedio et al., "Comparison of the Reaction Products of Oleic Acid Ozonized in BCl3-, HCl- and BF3-MeOH Media," Chemistry and Physics of Lipids 35(1):21-28 (1984) (Abstract only).
Office Action for U.S. Appl. No. 14/381,530, dated Dec. 10, 2015.

(56) References Cited

OTHER PUBLICATIONS

Gmehling et al., "Azeotropic Data for Binary Mixtures," Handbook of Chemistry and Physics (96th Edition) pp. 6-210 to 6-228 (2015-2016).
Akerman et al., "Biolubricant Synthesis Using Immobilised Lipase:Process Optimisation of Trimethylolpropane Oleate Production," Process Biochem. 46:2225-2231 (2011).
Office Action for U.S. Appl. No. 14/381,539, dated May 29, 2015.
Office Action for U.S. Appl. No. 14/381,554, dated Aug. 2, 2016.
Office Action for U.S. Appl. No. 14/381,564, dated Jun. 3, 2015.
Office Action (with English translation) for CN 201480024193.2, dated Aug. 17, 2016.
Extended search report for EP 14756526.1, dated Sep. 19, 2016.
Office Action for U.S. Appl. No. 14/381,554, dated May 3, 2017.
Office Action for U.S. Appl. No. 14/381,545, dated Jun. 2, 2017.

* cited by examiner

PREPARATION OF BIOPOLYOL ESTERS FOR LUBRICANT APPLICATION

This application is a national stage application under 35 U.S.C. 371 from PCT/MY2014/000026, filed Feb. 28, 2014, which claims the benefit of Malaysia Application No. PI 2013000713, filed Feb. 28, 2013, each of which is hereby incorporated by reference in its entirety.

FIELD OF THE INVENTION

The present invention relates to methods for the preparation of ester polyol esters for lubricant application. In particular, the ester polyol esters are prepared from the esterification reaction between ozone acids, typically derived from oxidative ozonolysis of fatty acids, and at least one primary polyol, such as trimethylolpropane (TMP) or glycerin. The resulting ester polyols produced from these reactions are then esterified with selected monoacid(s) to produce desired ester polyol esters. The ester polyol esters prepared in the present invention are particularly useful for use as synthetic base stock for lubricant applications.

BACKGROUND OF THE INVENTION

The listing or discussion of an apparently prior-published document in this specification should not necessarily be taken as an acknowledgement that the document is part of the state of the art or is common general knowledge.

The present invention is directed to a process to produce ester polyol esters (EPE) using renewable resources such as oils and fats, fatty acids, and fatty acid esters derived from plant and animal resources. These ester polyol esters are classified as Group V synthetic lubricant base stock and are particularly useful for use in high performance lubricant applications.

Group V lubricant base stocks include ester compounds and one type of high performance esters are polyol esters (PE) which are prepared by complete esterification of polyols such as TMP with monoacids. TMP trioleate is a common polyol ester formed from the esterification of the polyol TMP with oleic acid. Although Group V lubricant base stock technologies have demonstrated several performance advantages over traditional mineral oils, there is still room for further advancement or improvement in this field, especially with respect to enhancing performance characteristics of base stocks to extend the lubricant drain interval in high performance lubricant applications.

One of the common disadvantages of the commercially available polyol esters is related to high pour points, especially polyol esters produced from saturated fatty acids derived from tropical resources such as palm or coconut. Another disadvantage limiting performance is associated with the level of unsaturation where the double bonds in fatty acid components of polyol esters provide a point of attack for oxidation reactions to take place, which encourages oil degradation and precludes them for use in certain lubricant applications.

WO 2010/078505 discusses the preparation of ester polyols where the fatty acids derived from vegetable and/or animal oils are initially subjected to oxidative cleavage using ozone as the preferred cleavage reagent so that all double bonds are cleaved in a manner to generate carboxylic acid groups at each original double bonded carbon atom. In the oxidative ozonolysis of fatty acids derived from either vegetable oils or animal fats, a mixture of diacids and monoacids (referred to as ozone acids) are produced. The ozone acids are then esterified with select primary polyols such as TMP and/or other primary polyols to produce a wide range of polyol esters having a certain range of molecular weight and hydroxyl values.

In U.S. Pre-Grant Publication No. 2005/0112267, Yeong et al. concluded that common palm-based materials, especially palm olein or their ester derivatives developed for hydraulic application are only suitable for use in a tropical climate with temperatures ranging from 15° C. to 40° C. due to their high pour point.

The paper "Preparation and Characterization of Trimethylolpropane Esters from Palm Kernel Oil Methyl Esters" (Robiah et al., *Journal of Oil Palm Research*, 15(2), December 2003, pp. 42-49) reported that a lubricant base stock, i.e., TMP esters having an improved pour point in the range of 1° C. had been prepared from palm oil methyl ester (POME) and palm kernel oil methyl ester (PKOME). This improvement reflects that lubricant formulated with such esters can be used at a much lower temperature condition than reported previously. Malaysian Patent No. 140833 also filed by Robiah et al. discusses that the pour point of the TMP esters for the lubricant application can be reduced to a level of around −35° C. by removing via fractionation some of the saturated components in the ester mix. However, this separation step does not adequately remove all of the saturates to meet the most stringent requirement for pour point accepted by industry or original equipment manufacturers (OEMs).

U.S. 61/604,301 filed on 28 Feb. 2012 (not published yet) discloses a method for preparing ester polyols (EP) and ester polyol esters (EPE) and products therefrom. This method addresses some of the problems in the art. However, it was thought at the time of filing that the use of a two-step synthesis method instead of a one-step synthesis was beneficial, for example to produce products of superior performance characteristics (specifically higher molecular weight and lower volatility) and in a much shorter reaction time (60%), as compared to synthesis in a single step.

SUMMARY OF THE INVENTION

The present inventors have addressed some problems in the art and prepared ester polyol esters (EPE) particularly useful for use as synthetic base stock for lubricant applications.

In particular, it has now been found that the one-step method can be significantly quickened by using excess acid in the reaction mixture. On a laboratory scale of 250 g to 350 g, the average reaction time has been shown to be between 7.5-8 hours, which is comparable to the total reaction time of 7.25 hours taken for both steps used in the 2-step process. It is expected that the reaction time for the 1-step process will remain at 7.5-8 hours on larger scale (e.g. 77 L scale), provided that reaction apparatus capable of heating the reaction mixture at the same rate as on the laboratory scale is available. Further, it has been found that a one-step method which uses excess acid can be used to produce compounds useful as lubricants, over a wide range of viscosities while maintaining desirable characteristics such as low pour point and high oxidative stability. Therefore, it has been surprisingly found that a 1-step process is capable of being conducted at a comparable speed to the 2-step process and surprisingly produces lubricants that match, or exceed, the properties of the 2-step process.

The present invention therefore relates to a unique method of preparing ester polyols (EP) and ester polyol esters (EPE) and products therefrom.

In one aspect of the invention, there is provided a method for preparing an ester polyol ester, the method comprising preparing a reaction mixture comprising: at least one polyol compound, at least one dicarboxylic acid and at least one monocarboxylic acid, wherein the at least one polyol compound is esterified with the at least one dicarboxylic acid and the at least one monocarboxylic acid, wherein the reaction mixture has a hydroxyl group to carboxyl group ratio (HCR) corresponding to a ratio of moles of hydroxyl groups to moles of carboxyl groups, and the HCR is less than about 1.

In embodiments of the invention, the reaction mixture has a hydroxyl to carboxyl ratio (HCR) of less than about 0.97 (e.g. from about 0.92 to about 1, such as from about 0.92 to about 0.97, from about 0.93 to about 0.95, such as about 0.94).

In further embodiments of the invention, the carboxyl groups are present in a molar excess in comparison to the hydroxyl groups of from 5% to 30% (e.g. from 5.2% to 15%, such as from 5.3% to 6%).

In embodiments of the invention, the reaction mixture has the carboxyl groups in stoichiometric molar excess in comparison to the hydroxyl groups, wherein the molar excess of carboxyl groups in the reaction mixture provides an acid value (AV) of from about 11 mgKOH/g to about 40 mgKOH/g, optionally from about 12 mgKOH/g to about 30 mgKOH/g (e.g. from about 12 mgKOH/g to about 25 mgKOH/g, optionally from about 13 mgKOH/g to about 20 mgKOH/g, such as from about 16 mgKOH/g to about 18 mgKOH/g, e.g. about 18 mgKOH/g).

In embodiments of the invention, the reaction mixture has a difunctional/monofunctional Ratio (DMR) corresponding to a ratio of moles of dicarboxylic acid to moles of monocarboxylic acid and the compound has a viscosity proportional to the DMR of the reaction mixture.

In embodiments of the invention, a lubricant base stock is formed from the ester polyol ester; the lubricant base stock having volatility inversely proportional to the Difunctional/Monofunctional Ratio (DMR) of the reaction mixture.

In yet further embodiments of the invention, the method further comprises a catalyst, optionally wherein the catalyst is tin(II)oxide or tin(II)oxalate in a powder form in an amount from 0.01 wt % to 0.1 wt % of the reaction mixture.

In yet further embodiments of the invention, the carboxyl groups are present in a molar excess in comparison to the hydroxyl groups of from 5% to 30% (e.g. from 5.2% to 15%, such as from 5.3% to 6%).

In still yet further embodiments of the invention, the ester polyol ester produced by the esterification reaction is of Formula I:

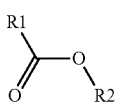

Formula I wherein R1 is a linear or branched alkyl chain having from 1 to 17 carbon atoms, optionally substituted with one or more hydroxyl groups, or R1 is a linear alkyl chain with from 2 to 18 carbon atoms and a terminal carboxylic acid group which is optionally esterified with a polyol compound of formula R2-OH;

R2, when attached to a hydroxyl group, is a linear or branched primary polyol having from 2 to 12 carbon atoms, wherein each alcohol functional group is optionally esterified with a monocarboxylic acid or dicarboxylic acid of formula R1-COOH, or a monocarboxylic acid of formula R3-COOH; and R3 is a linear or branched alkyl chain having from 1 to 17 carbon atoms, optionally substituted with one or more hydroxyl groups.

In embodiments of the invention, the ester polyol ester produced by the esterification reaction is of Formula II:

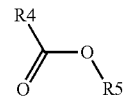

Formula II wherein R4 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, or R4 is a C2-C18 linear alkyl chain with a terminal carboxylic acid group which is optionally esterified with a polyol compound of formula R5-OH;

R5, when attached to a hydroxyl group, is the alkyl chain of a primary polyol selected from the group consisting of: glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol, wherein each alcohol functional group is optionally esterified with a monocarboxylic acid or dicarboxylic acid of formula R4-COOH, or a monocarboxylic acid of formula R6-COOH; and R6 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids.

In embodiments of the invention, the ester polyol ester produced by the esterification reaction is of Formula III:

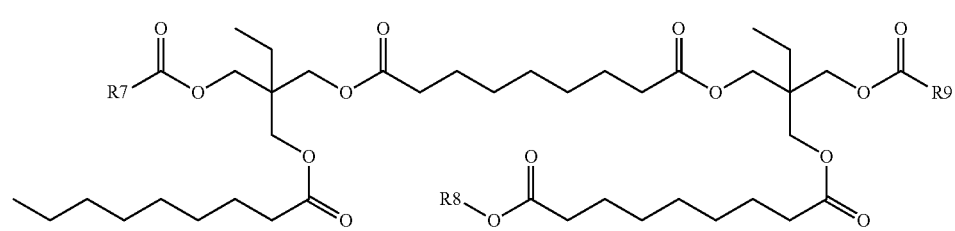

Formula III wherein R7, R8 and R9 are independently:
a linear or branched alkyl chain of between 1 to 17 carbon atoms, optionally substituted with one or more hydroxyl groups;
a C2-C18 linear alkyl chain with a terminal carboxylic acid group which is optionally esterified with a polyol compound of formula R10-OH; or
R10, wherein R10, when attached to a hydroxyl group, is a linear or branched primary polyol having from 2 to 12 carbon atoms and each alcohol functional group in R10 is optionally esterified with a linear or branched monocarboxylic acid having from 2 to 18 carbon atoms, or a dicarboxylic acid having from 2 to 18 carbon atoms.

In embodiments of the invention, the compound is of Formula IV:

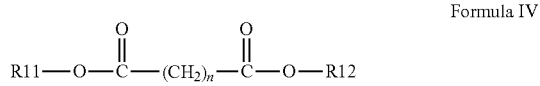

Formula IV wherein n is from 0 to 16;
R11 and R12, when each attached to a hydroxyl group, are independently a linear or branched primary polyol having from 2 to 12 carbon atoms, wherein each alcohol functional group is optionally esterified with a monocarboxylic acid of formula R13-COOH or dicarboxylic acid of formula R14-COOH;
R13 is a linear or branched alkyl chain having from 1 to 17 carbon atoms, optionally substituted with one or more hydroxyl groups; and
R14 is a C2-C18 linear alkyl chain with a terminal carboxylic acid group which is optionally esterified with a primary polyol compound of formula R11-OH or R12-OH.

In yet further embodiments of the invention, the at least one polyol compound is independently selected from the group consisting of: glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE), sorbitol and mixtures thereof (e.g. glycerin, trimethylolpropane (TMP), di-trimethylolpropane (Di-TMP), pentaerythritol (PE), sorbitol or mixtures thereof, such as trimethylolpropane).

In embodiments of the invention, the at least one monocarboxylic acid is selected from the group consisting of: acetic, propanoic, butyric, pentanoic, hexanoic, nonanoic, 2-ethyl hexanoic, heptanoic, octanoic, decanoic, lauric, myristic, palmitic, stearic acids and any combination thereof (e.g. hexanoic, nonanoic, 2-ethyl hexanoic, heptanoic, octanoic, decanoic and any combination thereof, such as nonanoic acid).

In embodiments of the invention, the at least one dicarboxylic acid is selected from Oxalic acid, Malonic acid, Succinic acid, Glutaric acid, Adipic acid, Pimelic acid, Suberic acid, Azelaic acid, Sebacic acid, 1,18-octadecanoic diacid and any combination thereof (e.g. azelaic, oxalic, malonic, 1,18-octadecanoic diacids and any combination thereof, such as azelaic acid).

In embodiments of the invention, the Difunctional/Monofunctional ratio (DMR) of the ozone acids (dicarboxylic and monocarboxylic acids) used in the process may be from about 0.01 to about 0.5 (e.g. from about 0.015 to about 0.3, such as from about 0.02 to about 0.26, e.g. 0.03 to about 0.24). The ester polyol ester may have a viscosity proportional to the Difunctional/Monofunctional Ratio (DMR) of ozone acids, and the viscosity at 40° C. of the ester polyol ester may be from about 10 cSt ($10^{-6}$ $m^2 \cdot s^{-1}$) to about 120 cSt ($10^{-6}$ $m^2 \cdot s^{-1}$) (e.g. 20 cSt ($10^{-6}$ $m^2 \cdot s^{-1}$) to about 110 cSt ($10^{-6}$ $m^2 \cdot s^{-1}$), such as 25 cSt ($10^{-6}$ $m^2 \cdot s^{-1}$) to about 105 cSt ($10^{-6}$ $m^2 \cdot s^{-1}$)).

The fatty acids used in the present invention may be in the form of a plurality or a mixture of fatty acids. In particular, the fatty acids may be derived from a mixture of fractionated palm fatty acid distillate (PFAD) and/or palm kernel fatty acid distillate In embodiments of the invention, the esterification reaction is considered complete when the reaction mixture has unreacted hydroxyl groups providing a hydroxyl value (HV) of less than about 10 mgKOH/g (e.g. less than about 8 mgKOH/g, less than about 6 mgKOH/g or less than about 5 mgKOH/g).

In yet further embodiments of the invention, the at least one monocarboxylic acid and/or the at least one dicarboxylic acid is prepared by reacting at least one fatty acid with ozone followed by oxidation. For example, the at least one fatty acid is produced by hydrolyzing at least one triglyceride and the the at least one triglyceride comprises at least one vegetable oil and/or at least one animal fat (e.g. selected from the group consisting of: fish oil, tallow, duck fat, and a mixture thereof).

In still yet further embodiments of the invention, the at least one vegetable oil is selected from the group consisting of: soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, palm and palm kernel oils, palm olein, and a mixture thereof (e.g. palm oil, palm olein, palm kernel oil).

In still yet further embodiments of the invention, the at least one fatty acid is derived from fractionated palm fatty acid distillate (PFAD) or palm kernel fatty acid distillate (PFKAD).

In further embodiments of the invention, the method further comprises purification of the ester polyol ester, said purification comprising:
(a) contacting the crude reaction product with an aqueous solution containing an alkaline compound and a de-emulsifier to generate a mixture;
(b) subjecting the mixture to a mixing phase, comprising stirring the mixture for at least 3 minutes to form a soap-in-oil suspension, optionally the mixing phase is conducted at ambient temperature for up to 10 minutes (e.g. up to 5 minutes);
(c) delivering the soap-in-oil suspension to a centrifuge at an optimum temperature to break soap-in-oil suspension and collection of the ester polyol ester;
(d) subjecting the collected ester polyol ester to a Montmorillonite clay adsorbent treatment to remove any catalyst remaining in the ester polyol ester, optionally wherein the ester polyol ester and the clay are maintained at optimum temperatures; and
(e) collecting the purified ester polyol ester.

In further embodiments of the invention, the molar excess of carboxyl groups in the reaction mixture following purification provides an acid value (AV) of less than about 1 mgKOH/g (e.g. less than about 0.7 mgKOH/g).

In still yet further embodiments of the invention, the HCR is about 0.94; the AV is less than 1 mgKOH/g following purification of the product; the DMR is about 0.03; the at least one fatty acid is derived from palm fatty acids; and the ester polyol ester has a kinematic viscosity at 40° C. of about 25 cSt ($10^{-6}$ $m^2 \cdot s^{-1}$).

In yet further embodiments of the invention, the HCR is about 0.95; the AV is less than 1 mgKOH/g following purification of the product; the DMR is about 0.12; the at least one fatty acid is derived from palm fatty acids; and the ester polyol ester has a kinematic viscosity at 40° C. of about 44 cSt ($10^{-6}$ $m^2 \cdot s^{-1}$).

In still yet further embodiments of the invention, the HCR is about 0.95; the AV is less than 1 mgKOH/g; the DMR is about 0.24; the at least one fatty acid is derived from palm fatty acids; and the ester polyol ester has a kinematic viscosity at 40° C. of about 105 cSt ($10^{-6}$ $m^2 \cdot s^{-1}$).

Selective DMR and HCR ratios may influence the properties of lubricant base stock. For example, an increased ratio of DMR results in increased molecular weight causing an increased viscosity and decreased volatility. An increased ratio of HCR results in decreased molecular weight causing a decrease in viscosity and increase in volatility.

There is also provided an ester polyol ester obtainable or obtained according to any method to the invention. There is also provided an ester polyol ester lubricant base oil comprising the ester polyol ester according to the invention.

According to another aspect, there is provided an ester polyol ester lubricant base oil, comprising the reaction product of:
at least one carboxylic acid; and
at least one ester polyol,
wherein the ester polyol has at least one ester group, a first hydroxyl group, and at least a second hydroxyl group, The ester polyol ester lubricant base oil according to any aspect of the invention having a pour point from about –10° C. to about –70° C. (e.g. –40° C. to about –60° C., such as –48° C. to about –57° C.).

The ester polyol esters of the present invention are unique because they have lower pour points than pour points of typical biobased lubricant basestocks within the same viscosity range. Further, they may be produced conveniently and economically from a one-step synthesis using a range of biobased feedstock. This invention also provides a means to produce a broader range of kinematic viscosity profiles at 40° C. ranging from 10 cSt to 200 cSt, while maintaining an appreciably lower volatility, which indirectly reflects good thermal stability. Low pour points may eliminate or reduce the need for pour point depressants (PPDs), while the broader viscosity profiles will minimize or eliminate the need of adding polymeric viscosity modifiers in lubricant formulations. These advantages will greatly broaden the applicability of ester polyol esters.

The structures of the ester polyol esters of the present invention are also different than the conventional polyol esters, and this structural uniqueness is transferred to performance advantages. The structural distinctiveness can be related to the unsymmetrical arrangement of their molecular structure where different proportions of diacid and/or monoacids react with any one primary polyols during esterification. The resulting diversity of structures hinders close packing of the polyol ester chains and thus inhibits crystallization. This is another advantage with respect to maintaining the ester polyol ester fluidity, especially when preparing the polyols from tropical feedstock, such as, palm or coconut that contain high amounts of high melting palmitic and stearic acids.

BRIEF DESCRIPTION OF THE FIGURES

The accompanying figures, which are incorporated in and constitute a part of this specification, illustrate aspects of the invention and, together with a general description of the invention given above, and the detailed description given below, serve to explain the invention.

DETAILED DESCRIPTION OF THE INVENTION

Bibliographic references mentioned in the present specification are for convenience listed in the form of a list of references and added at the end of the examples. The whole content of such bibliographic references is herein incorporated by reference.

The present invention relates to a method of forming ester polyol esters (EPE) from ozone acids.

The ester polyol ester according to any aspect of the invention comprises the structure:

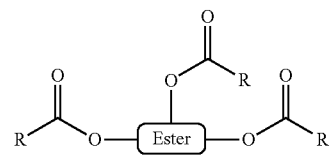

Figure 5:
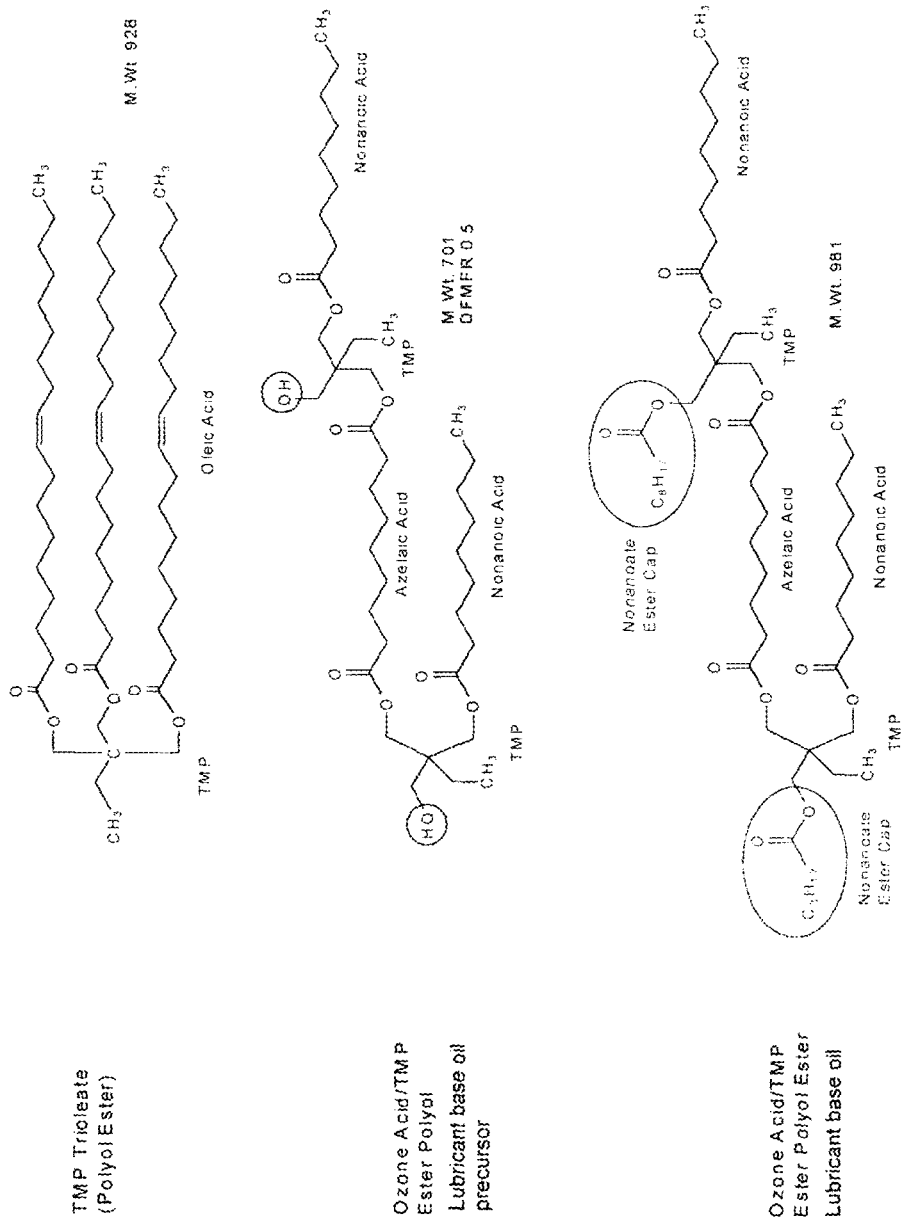
FIG. 5 illustrates the structures of the polyol ester TMP trioleate, an intermediate ester polyol lubricant base oil precursor, and an ester polyol ester lubricant base oil.
Figure 6:
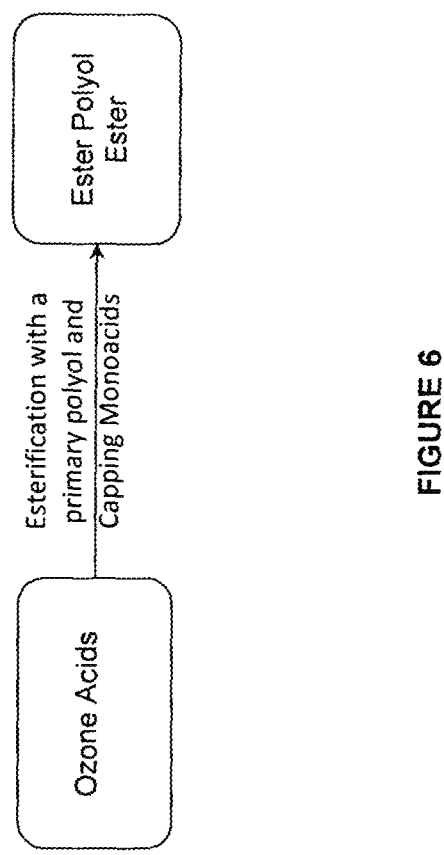
FIG. 6 is a simplified block diagram illustrating the one-step synthesis method of producing an ester polyol ester compound according to the present invention.
Figure 7:
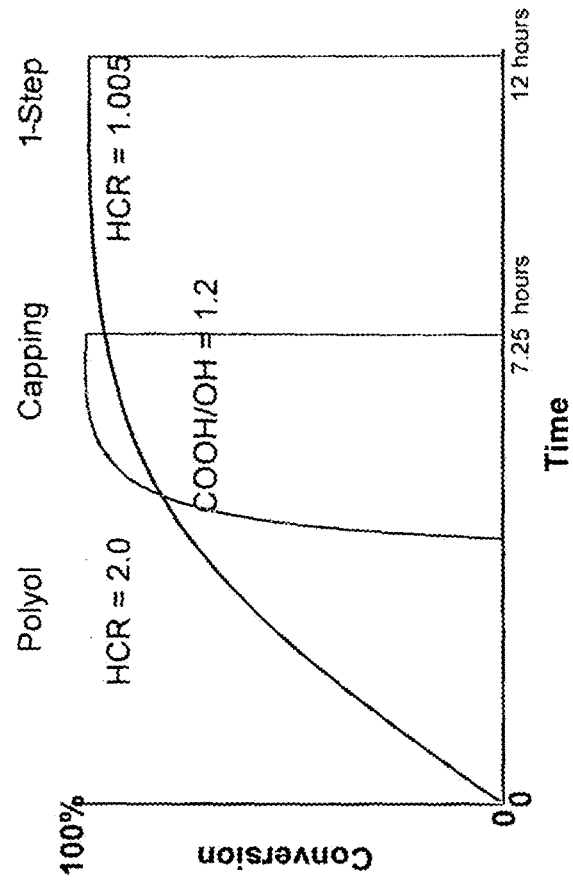
FIG. 7 is a graph illustrating the differences in reaction time and reactant concentration of the two-step synthesis versus the one-step synthesis of a ester polyol ester without using excess acid.

An example of a compound according to any aspect of the invention is provided in FIG. 5, with a reaction intermediate denoted as a precursor.

When used in embodiments and aspects of the invention, the term "ozone acid mixture" refers to a mixture of the at least one dicarboxylic acid and at least one monocarboxylic acid.

When used in embodiments and aspects of the invention, the "ester polyol reaction mixture" refers to a mixture of the at least one primary polyol, the at least one dicarboxylic acid and at least one monocarboxylic acid. It is used interchangeably with "reaction mixture".

When used in embodiments and aspects of the invention, the term "comprises" and variants thereof can be replaced by the term "consists" and variants thereof and vice versa.

When used in embodiments and aspects of the invention, "azelaic acid" may refer to pure, that is 97-100% pure azelaic acid, or it may contain up to 8% of other diacids and up to 15% of monocarboxylic acids.

When used in embodiments and aspects of the invention, "pelargonic acid" may refer to pure, that is 97-100% pure pelargonic acid, or it may contain up to 16% of other monocarboxylic acids.

The primary polyol according to any aspect of the invention may be selected from glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol. More in particular, the primary polyol may be a branched polyhydric primary polyol. More in particular, the primary polyol may be trimethylolpropane (TMP).

In one particular aspect of the invention, the ester polyol ester viscosity may be proportional to the Difunctional/Monofunctional Ratio (DMR) of the ozone acid mixture.

In one particular aspect of the invention, a lubricant base stock may be formed from the ester polyol ester; the lubricant base stock having a volatility that may be inversely proportional to the Difunctional/Monofunctional Ratio (DMR) of the ozone acid mixture.

In one particular aspect of the invention, the method may further comprise increasing the Difunctional/Monofunctional ratio (DMR) of the ozone acid mixture, thereby decreasing the volatility of the lubricant base stock.

In one particular aspect of the invention, the method may further comprise increasing the Difunctional/Monofunctional ratio (DMR) of the ozone acid mixture, thereby increasing the viscosity of the lubricant base stock.

In one particular aspect of the invention, the ester polyol ester may have a molecular weight (GPC) proportional to the Difunctional/Monofunctional Ratio (DMR) of the ozone acid mixture.

In one particular aspect of the invention, the one or more additional second monocarboxylic acids may be selected from the group consisting of: acetic, propanoic, butyric, pentanoic, hexanoic, nonanoic, 2-ethyl hexanoic, heptanoic, octanoic, decanoic, lauric, myristic, palmitic and stearic acids, and mixtures thereof. More in particular, the one or more additional second monocarboxylic acids may be selected from the group consisting of: hexanoic, nonanoic, 2-ethyl hexanoic, heptanoic, and octanoic acids.

The at least one fatty acid according to any aspect of the invention may be produced by hydrolyzing at least one triglyceride. In particular, the at least one triglyceride may comprise at least one vegetable oil and/or at least one animal fat. More in particular, the at least one vegetable oil may be selected from the group consisting of: soybean, safflower, linseed, corn, sunflower, olive, canola, sesame, cottonseed, mustard, camelina, jatropha, peanut, coconut, rapeseed, Chinese tallow, tung, castor, algae, wheat germ, soya, hemp, palm and palm kernel oils, palm olein, and a mixture thereof. More in particular, the at least one vegetable oil may comprise palm oil. In one particular aspect of the invention, the at least one vegetable oil may comprise palm olein. In one particular aspect of the invention, the at least one vegetable oil may comprise palm kernel oil. In one particular aspect of the invention, the at least one fatty acid may be derived from fractionated palm fatty acid distillate (PFAD). In one particular aspect of the invention, the at least one fatty acid may be derived from fractionated palm olein. In one particular aspect of the invention, the at least one fatty acid may be derived from palm kernel fatty acid distillate (PFKAD). In one particular aspect of the invention, the at least one animal fat may be selected from the group consisting of: fish oil, tallow, duck fat, and a mixture thereof.

In particular, the method of the present invention preferably utilizes ozone acids produced from an oxidative ozonolysis process. More in particular, fatty acids, preferably derived from vegetable oil and/or animal oils, are initially subjected to oxidative cleavage so that all double bonds are cleaved and converted to carboxylic acid groups. In the oxidative cleavage of unsaturated fatty acids derived from vegetable oil or animal oils, a mixture of a diacid (azelaic acid) and monoacids (the mixture referred to as ozone acids) is produced.

According to one aspect of the present invention one or more fatty acids, for example a plurality or mixture of fatty acids, may be reacted with ozone to produce a mixture of ozone acids. The obtained ozone acids or mixture of ozone acids may comprise diacid and monoacid compounds. In particular, the (mixture of) ozone acids may have a Difunctional/Monofunctional Ratio (DMR) corresponding to a ratio of moles of diacid to moles of monoacid. The ozone acids are then esterified with primary polyols, such as but not limited to, neopentyl glycol (NPG), trimethylolpropane (TMP), pentaerythritol (PE), ditrimethylolpropane, dipentaerythritol, and the like, to form ester polyols. The resultant ester polyols are then esterified with at least one carboxylic acid to generate a unique class of ester polyol esters suitable for use as lubricant base stock.

Figure 4:
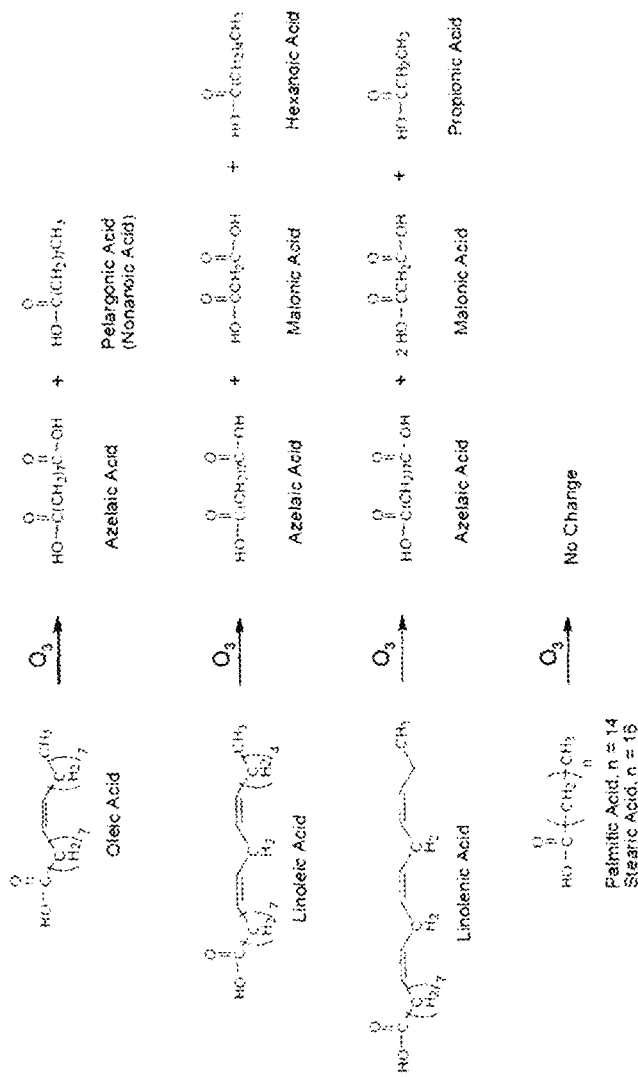
FIG. 4 illustrates the specific ozone acids formed by the oxidative ozonolysis of different fatty acids.

FIG. 4 illustrates the oxidative cleavage of representative fatty acids to produce specific mixtures of ozone acids. In this Figure, oleic acid is converted to azelaic acid and pelargonic acid (nonanoic acid); linoleic acid is converted to azelaic, hexanoic and acetic acids, and linolenic acid is converted to azelaic, acetic and propanoic acids. Acetic acid is formed from the decarboxylation of malonic acid under the combined oxidative ozonolysis reaction conditions. The saturated fatty acids such as palmitic and stearic acids remain unchanged.

Triglycerides such as palm oil, palm fatty acid distillates (PFAD), and palm kernel fatty acid distillates (PKFAD) or their alkyl esters can be hydrolyzed to produce fatty acids which serve as feedstocks for oxidative ozonolysis.

Examples of triglycerides include vegetable oil and animal fat. In particular, the triglyceride may be selected from palm oil, olein, soybean oil, safflower oil, linseed oil, corn oil, sunflower oil, olive oil, canola oil, sesame oil, cottonseed oil, mustard oil, camelina oil, jatropha oil, peanut oil, coconut oil, rapeseed oil, Chinese tallow oil, tung oil, castor oil, algae oil, wheat germ oil, soya oil, hemp oil, fish oil, tallow, duck fat, or the like, and a mixture thereof.

Sources of fatty acids include palm fatty acid distillate, fractionated palm fatty acid distillate, palm kernel fatty acid distillate, fractionated palm kernel fatty acid distillate, phospholipids, soybean oil fatty acid esters, palm oil fatty acid esters, phospholipids, or the like, or a mixture, or a fraction thereof.

Figure 1:
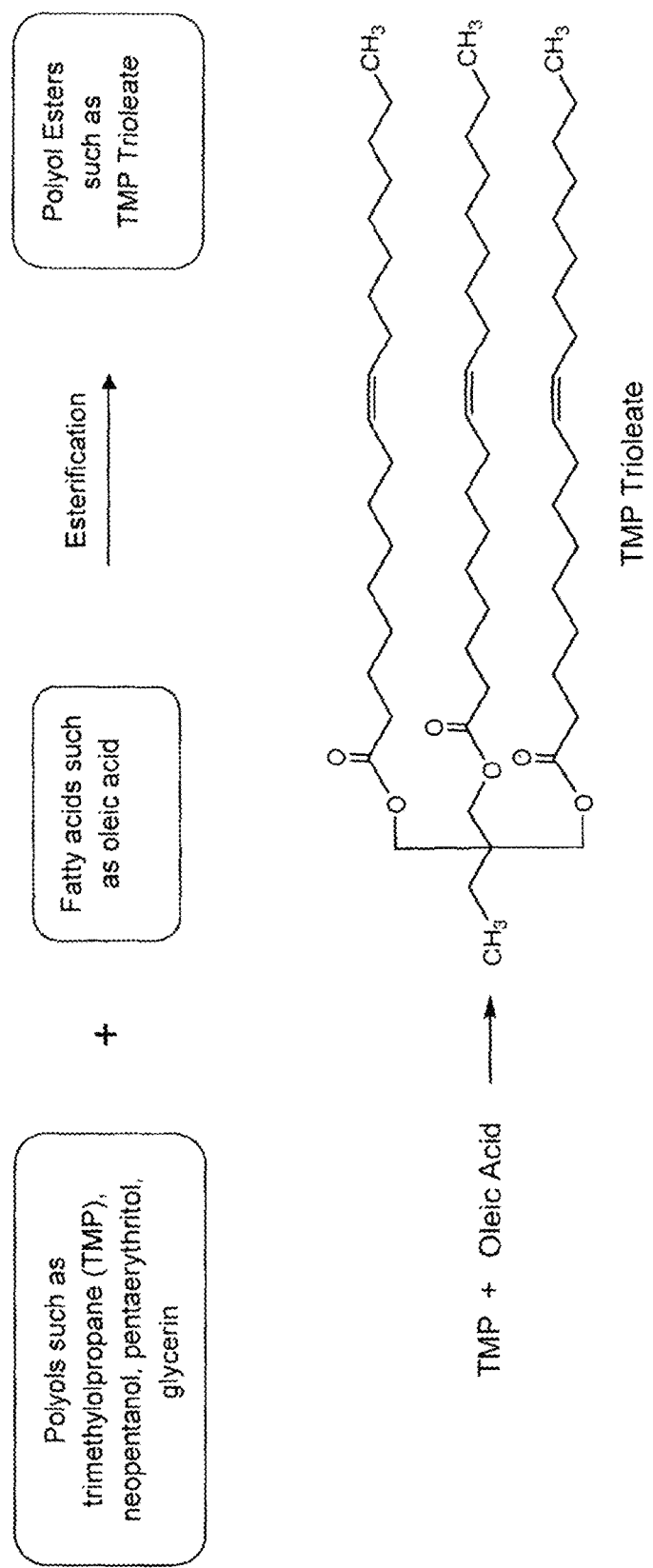
FIG. 1 shows the esterification of fatty acids such as oleic acid with polyols such as trimethylolpropane (TMP) to produce conventional polyol esters (PE) such as TMP trioleate.
Figure 2:
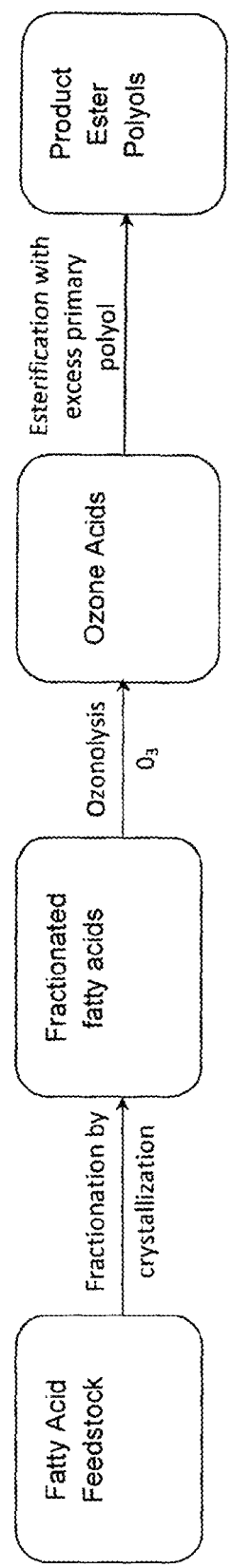
FIG. 2 is a simplified block diagram illustrating the conventional process of producing a mixture of ozone acids by ozonolysis of fractionated fatty acids and their esterification with excess primary polyol to form intermediate ester polyols (EP). The fatty acid feedstock in the simplified block diagram of FIG. 2 may be composed of vegetable oils, animal fats, fatty acids, and/or fatty acid esters optionally fractionated to reduce the saturated fatty acid content in the fractionated fatty acids. The fractionated fatty acids undergo a solvent-based oxidative ozonolysis reaction to produce ozone acids. The ozone acids are then esterified with excess primary polyol, e.g., glycerin to produce the product ester polyols.

FIG. 2 shows a simplified block diagram illustrating the conventional process of producing ester polyols via ozonolysis of fractionated fatty acids to form a mixture of ozone acids. The fatty acids are formed from the hydrolysis of triglyceride or fatty acid ester feedstock. The second-step of the conventional process is esterification of the ozone acids with excess primary polyol, typically TMP or glycerin, to form product ester polyols.

Figure 3:
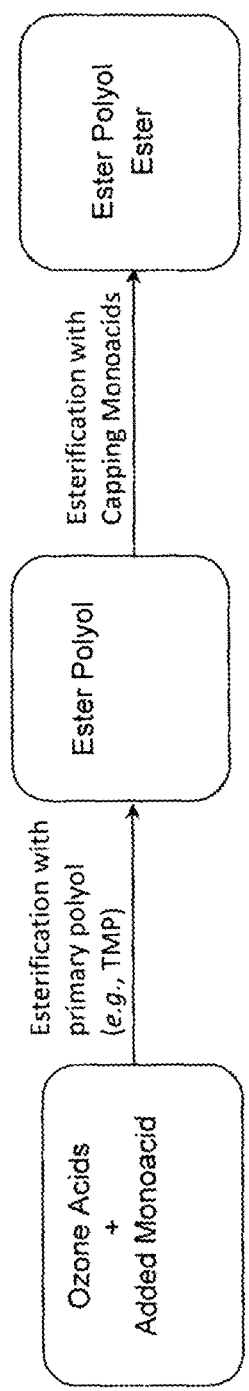
FIG. 3 shows the two-step conversion of ozone acids to lubricant base oil composed of the ester polyol esters.

In FIG. 3, according to one aspect of the invention, mixtures of ozone acids and optional monofunctional carboxylic acids (monoacids) are esterified with primary polyols such as TMP to form ester polyols. By "primary polyol" we mean a polyol having two or more hydroxyl groups which can be used as a reactant in various processes. For example, the primary polyol can be used as a reactant in an ozonolysis process that uses at least one of its hydroxyl groups in forming ester linkages to fatty acid components in generating the secondary polyol, or as a reactant in an esterification process of an oxidation acid. The primary polyol may include glycerin, diglycerin, ethylene glycol, diethylene glycol, 1,2-propanediol, bis(1,2-propanediol), 2-methyl-1,3-propanediol (2-MePG); trimethylolpropane (TMP); di-trimethylolpropane (Di-TMP); neopentyl glycol (NPG); pentaerythritol (PE); dipentaerythritol (diPE); and sorbitol.

Ester polyol esters in the present invention can be used widely for lubricant base stocks.

Examples of monocarboxylic acids include acetic, propanoic, butyric, pentanoic, hexanoic, heptanoic, octanoic, 2-ethylhexanoic, nonanoic, decanoic, lauric, myristic, palmitic and stearic acids and mixtures, thereof.

According to one aspect of the invention, the ester polyols and ester polyol esters of the present invention may incorporate branched primary polyols. The branched primary polyols are effective in inhibiting phase separation in hydrocarbon chains, particularly from palm feedstock because palm feedstock contains high amounts of saturated fatty acids that cause phase separation. An example of a branched primary polyol is Trimethylolpropane (TMP) that is shown below.

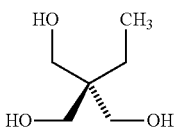

Branched primary polyols may be selected from 1,2-propanediol; 2-methyl-1,3-propanediol (2-MePG); trimethylolpropane (TMP); di-trimethylolpropane (Di-TMP); or neopentyl glycol (NPG). Following the esterification of the ozone acids, the product ester polyols are esterified with carboxylic acid to produce ester polyol esters.

In particular, the ester polyol ester may have a repeated group (RCO$_2$R') where R represents palmitate, stearate, hexanoate, nonanoate (pelargonate), propionate and azelate (as di-esters) derived from the ozone acids. R' is derived from primary polyols.

Accordingly, in an embodiment, the ester polyol esters may be linear structures. In another embodiment, the ester polyol esters may be branched structures. Both may incorporate a branched primary polyols. The structure of the ester branched polyol esters hinders the close packing of hydrocarbon chains, which inhibits crystallization.

Esterification reactions according to any aspect of the present invention may be catalyzed by tin oxalate or tin oxide catalyst.

In an aspect of the present invention, lubricant compositions are prepared from "synthetic" ozone acid mixtures expected to be produced from oxidative ozonolysis of a range of fatty acid-containing feedstocks. It is known that oxidative ozonolysis of fatty acids as specified by U.S. Pat. No. 2,813,113 and related patents results in generation of carboxylic acid functionality at each of the two carbon atoms that originally comprise the double bonds of each fatty acid before undergoing oxidative cleavage. Examples of individual ozone acids produced from the oxidative ozonolysis of select individual fatty acids are illustrated in FIG. 3. This knowledge allows one to calculate and predict the specific percentages of the diacid azelaic acid and all monoacids resulting from oxidative ozonolysis of any fatty acid feedstock composition. Accordingly, all lubricant compositions described herein were prepared from specific diacid and monoacids expected to be produced from oxidative ozonolysis of a range of fatty acid-containing feedstocks. Different ozone acid compositions were prepared by mixing together the calculated amounts of diacid (e.g., azelaic acid) and monoacids using purchased high-purity compounds. We refer to these "synthetic" ozone acid mixtures as simulated ozone acids. Two specific sets of simulated ozone acids were extensively used in the development and these were derived from PFAD and Edenor OL-72. (a) PFAD represents the ozone acids expected from palm oil fatty acid distillate (12% palmitic acid, 1.5% myristic acid, 68% oleic acid, and 16% linoleic acid) which results in a DMR of 0.71 (b) Edenor OL-72 represents an ozone acid mixture expected from olein that had been purified to contain nominally 72 percent oleic acid and the specific composition that was simulated contained 75.6% oleic acid, 11.4% linoleic acid, 4.41% palmitic, 2.8% stearic acid and 4.5% myristic acid which resulted in ozone acids with a DMR of 0.762.

An advantage of this approach is that we were able to prepare specific ozone acid compositions predicted to result from any fatty acid feedstock available worldwide. On the other hand, only one ozone acid composition is commercially available and that composition results from the oxidative ozonolysis of a specific fatty acid mixture obtained from purified tallow.

One specific simulated ozone acid mixture used to prepare the ester polyols was the mixture predicted to be obtained from the oxidative ozonolysis of palm based fatty acid. The compositions of the simulated ozone acid mixtures derived from PFAD, fractionated PFAD, palm kernel fatty acid distillate (PKFAD), and the ozone acid mixture derived from partially purified olein such as Edenor OL-72 (produced by Emery Oleochemicals) were predicted knowing the specific fatty acid composition of each feedstock. Edenor OL-72 is a fatty acid mixture containing about 72% oleic acid content. Any suitable fatty acid mixture having a high oleic content may be used as the feedstock for ozone acids. Preferably, an ozone acid mixture with a high percentage of oleic acid is used because it results in a lower percentage of saturated fatty acids.

The lubricant base stock of the present invention has improved physical properties, such as, viscosity, pour point, and molecular weight. The ability to correlate changes to the polyol structure with differences in the performance properties is a feature of the present invention. By changing compositional factors, such as the amount and composition of ozonolysis feedstock, primary polyols and any additional acids added, we can adjust the properties of ester polyol ester and thus the lubricant base oil. The specific combination of these compositional factors establishes key parameters known as the carboxylic acid difunctional to monofunctional ratio (DMR) and the hydroxyl to carboxyl ratio (HCR), which dictate the structure of intermediate ester polyols.

These selective ratios are critical factors in providing unique characteristics in terms of superior performance in low temperature fluidity, thermal stability, and broader viscosity profiles of lubricant base stocks. The difunctional to monofunctional ratio (DMR) of the ozone acids is critical in achieving the desired polyol ester molecular weights, which results in achieving the targeted ester polyol ester viscosity and volatility. The viscosity, volatility, and molecular weight of the ester polyol esters are also found to be dependent on the DMR of the reaction mixture, e.g. ozone acids and any extra acids that may be added. This proves to be vital in terms of the usage of the ester polyol esters for high performance lubricant applications.

The present invention will also show that modifying the hydroxyl to carboxyl ratio (HCR) has an effect towards adjusting the ester polyol ester viscosity.

An object of the present invention is to demonstrate variations in viscosities, pour points, and/or volatilities of the ester polyol esters and dependence of these properties on the compositional properties of the ester polyols from which they are derived. A major factor that influences the ester polyol and ester polyol ester viscosities is the DMR of the ozone acid mixtures used to prepare the ester polyols. The DMR is the ratio of the molar amount of diacid to monoacids in the ozone acid or ozone acid mixtures that can also include added monoacids as needed. The use of higher DMR feedstocks results in increased ester polyol and ester polyol ester viscosities and decreased volatilities. Conversely, a decreased DMR feedstock results in decreased ester polyol component molecular weights, resulting in decreased viscosities and increased volatilities of the ester polyols and ester polyol esters.

FIG. 5 shows structures of the polyol ester TMP trioleate (top), lubricant ester polyol base oil precursor formed by the esterification reaction of select ozone acids with TMP (middle), and ester polyol ester formed by the esterification reaction of ester polyol lubricant base oil precursor (bottom). The middle structure in FIG. 5 is the lubricant base oil precursor formed after the first-step of the two-step conversion of the ozone acid with the primary polyol TMP in the present invention. The bottom structure in FIG. 5 is the lubricant base oil or ester polyol ester of the present invention formed after the ester polyol is esterified with capping monoacids. In this example, the hydroxyl groups of the ester polyol are esterified by nonanoic acid, also named pelargonic acid. Nonanoic acid is a typical capping monoacid used during the second esterification step of a two-step process for preparing ester polyol ester. It may also be included in the reaction mixture for the one-step esterification method of the present invention. The final structure is an ester polyol ester, which is used as a lubricant base oil.

The DMR is a key parameter in controlling lubricant basestock viscosity and volatility. Since the only difunctional acid resulting from oxidative ozonolysis of unsaturated fatty acids is azelaic acid, it can be seen that DMR ratios will be higher the higher the feedstock unsaturation level and lower the lower the feedstock unsaturation level. Based on the composition of fractionated PFAD, the DMR of the ozone acid composition resulting from oxidative ozonolysis of fractionated PFAD is 0.71. By comparison, the DMR of the ozone acids resulting from oxidative ozonolysis of soybean oil fatty acids has a value of 1.51 due to the increased level of unsaturation in soybean oil. The DMR of any ozone acid composition may be adjusted downward as necessary by the addition of monoacids to access compositional ranges of a polyol which suits the lubricant base stock. In general, increased DMR values indicate increased amounts of azelaic acid that favors the formation of higher molecular weight structures and more crosslinked structures in the presence of trifunctional or higher functionality primary polyols. These molecular effects result in higher viscosities and lower volatilities.

In the ester polyols, increased amounts of primary polyol hydroxyl functionality relative to available carboxyl functionality results in increased HCR values and increased hydroxyl functionality after esterification. Thus, the higher the amount of primary polyol relative to carboxyl functionality as measured by increased HCR, the higher the resulting hydroxyl value (HV) of intermediate ester polyols. The viscosities of resulting ester polyols and ester polyol esters are also expected to increase as the HCR is reduced. This is because a reduction in HCR leads to increased incorporation of the primary polyol hydroxyl groups leading to increased molecular weights if the primary polyol has two hydroxyl groups and increased crosslinking if the primary polyol has three or more hydroxyl groups. Thus, control of the feedstock DMR, which is characteristic of different ozone acid feedstocks and which can be readily reduced by addition of external monoacids, and HCR as well as choice of primary polyols can be used to produce a wide range of ester polyol esters lubricant base stocks having varying structure, viscosities, and volatilities.

The esterification of appropriate palm-based ester polyols with monoacids produced lubricant base oil with appropriate ranges of viscosities, pour points, and volatilization properties. Without such ester polyol esterification, critical performance properties would not be achieved for most lubricant applications.

When using TMP as the primary polyol, the ISO viscosities, which are viscosities measured in centistokes (abbreviated cS) at 40° C. of ester polyol esters were strongly dependent on the DMR of the ozone acid feedstock used to prepare intermediate ester polyols. This feature is understandable on a molecular basis since higher amounts of difunctional acids will give rise to increased crosslinking between TMP (which contains three hydroxyl groups per molecule) resulting in higher lubricant base oil viscosities. Conversely, increased amounts of monofunctional acids, which results in lower DMR will block the relative ability of TMP to undergo crosslinking involving TMP due to blocking one or more of TMP hydroxyl groups with monoacid esters, leading to decreased viscosities.

According to one aspect, the present invention provides an ester polyol ester obtained or obtainable by the above methods According to one aspect, the present invention provides an ester polyol ester lubricant base oil comprising the ester polyol ester obtained or obtainable by the above methods According to one aspect, the present invention provides an ester polyol ester lubricant base oil comprising the reaction product of at least one carboxylic acid and at least one ester polyol, wherein the ester polyol may have at least one ester group, a first hydroxyl group, and at least a second hydroxyl group. The ester polyol ester lubricant base oil may have a molecular weight (GPC) of about 700-1900 g/mol. The at least one carboxylic acid may be selected from the group consisting of: acetic, propanoic, butyric, pentanoic, hexanoic, nonanoic, 2-ethyl hexanoic, heptanoic, octanoic, decanoic, lauric, myristic, palmitic and stearic acids, and mixtures thereof. In particular, the at least one carboxylic acid may be nonanoic acid. The ester polyol ester lubricant base oil may have a pour point of below about −11.0° C. In particular, the ester polyol ester lubricant base oil may have a pour point of between about −57.0° C. to about −11.0° C.

According to one aspect, the present invention provides an ester polyol ester composition comprising a compound of Formula I:

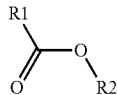

Formula I wherein R1 is a linear or branched alkyl chain having from 1 to 17 carbon atoms, optionally substituted with one or more hydroxyl groups, or
R1 is a linear alkyl chain with from 2 to 18 carbon atoms and a terminal carboxylic acid group which isoptionally esterified with a polyol compound of formula R2-OH;
R2, when attached to a hydroxyl group, is a linear or branched primary polyol having from 2 to 12 carbon atoms, wherein each alcohol functional group is optionally esterified with a monocarboxylic acid or dicarboxylic acid of formula R1-COOH, or a monocarboxylic acid of formula R3-COOH; and
R3 is a linear or branched alkyl chain having from 1 to 17 carbon atoms, optionally substituted with one or more hydroxyl groups.

According to one aspect, the present invention provides an ester polyol ester composition comprising a compound of Formula II:

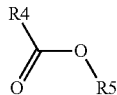

Formula II wherein R4 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids, or
R4 is a C2-C18 linear alkyl chain with a terminal carboxylic acid group which is optionally esterified with a polyol compound of formula R5-OH;
R5, when attached to a hydroxyl group, is the alkyl chain of a primary polyol selected from the group consisting of: glycerin, diglycerin, ethylene glycol, diethylene glycol, 1,2-propanediol, bis(1,2-propanediol), 2-methyl-1,3-propanediol (2-MePG), trimethylolpropane (TMP), di-trimethylolpropane (Di-TMP), neopentyl glycol (NPG), pentaerythritol (PE), dipentaerythritol (diPE) and sorbitol, wherein each alcohol functional group is optionally esterified with a monocarboxylic acid or dicarboxylic acid of formula R4-COOH, or a monocarboxylic acid of formula R6-COOH; and
R6 is the alkyl chain of a monocarboxylic acid selected from the group consisting of: acetic, propanoic, butyric, pentanoic, hexanoic, nonanoic, 2-ethyl hexanoic, heptanoic, octanoic acid, decanoic, lauric, myristic, palmitic and stearic acids.

According to one aspect, the present invention provides an ester polyol ester composition comprising a compound of Formula III:

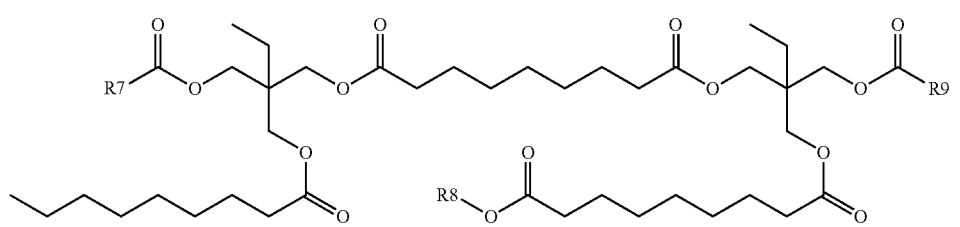

Formula III wherein R7, R8 and R9 are independently:
a linear or branched alkyl chain of between 1 to 17 carbon atoms, optionally substituted with one or more hydroxyl groups;
a C2-C18 linear alkyl chain with a terminal carboxylic acid group which is optionally esterified with a polyol compound of formula R10-OH; or
R10, wherein R10, when attached to a hydroxyl group, is a linear or branched primary polyol having from 2 to 12 carbon atoms and each alcohol functional group in R10 is optionally esterified with a linear or branched monocarboxylic acid having from 2 to 18 carbon atoms, or a dicarboxylic acid having from 3 to 9 carbon atoms.

According to one aspect, the present invention provides an ester polyol ester composition comprising a compound of Formula IV:

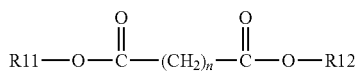

Formula IV wherein n is from 0 to 16;
R11 and R12, when each attached to a hydroxyl group, are independently a linear or branched primary polyol having from 2 to 12 carbon atoms, wherein each alcohol functional group is optionally esterified with a monocarboxylic acid of formula R13-COOH or dicarboxylic acid of formula R14-COOH;
R13 is a linear or branched alkyl chain having from 1 to 17 carbon atoms, optionally substituted with one or more hydroxyl groups; and
R14 is a C2-C18 linear alkyl chain with a terminal carboxylic acid group which is optionally esterified with a primary polyol compound of formula R11-OH or R12-OH.

Table A shows viscosities for ester polyol esters prepared using a two-step esterification process.

TABLE A

Ester Polyol Ester Viscosities versus HCR at DMR of 0.12 After Capping Polyol Esters with Nonanoic Acid

| LRB No. | | DMR | HCR | Viscosity (cP) |
|---|---|---|---|---|
| 52921-22-28 | PKFAD | 0.12 | 1.15 | 50.84 |
| 52921-2-32 | PKFAD | 0.12 | 1.25 | 45.97 |
| 52921-19-31 | PKFAD | 0.12 | 1.35 | 41.65 |
| 52921-38-29 | PFAD & Nonanoic acid | 0.11 | 1.25 | 35.09 |
| 52921-40-29 | PFAD & Nonanoic acid | 0.11 | 1.35 | 33.69 |

From the above, it can be seen that the viscosities of lubricant base oil candidates can be adjusted to desired values by adjusting either the DMR and HCR of the polyol used to prepare the final base oil when followed by capping with monoacids, such as, nonanoic acid. This allows producers to obtain a variety of base oil ISO viscosities by independent adjustment of the parameters or adjustment in concert with each other to obtain desired viscosities.

TABLE B

TMP-Based Lubricant Base Oil Properties at Increased DMR and HCR

| Exp. No. | Simulated Ozone Acids[a] | DMR | HCR | Viscosity @ 40° C. (cS) | Pour Point (° C.) | Percent Simulated Composition of Ozone Acids |
|---|---|---|---|---|---|---|
| 1 | Edenor OL-72 + Non. Acid[b] | 0.134 | 1.25 | 56 | −54 | — |
| 2 | Edenor OL-72 + Non. Acid[b] | 0.40 | 2.0 | 49 | −54 | 23.0 |
| 3 | Edenor OL-72 + Non. Acid[b] | 0.60 | 2.0 | 69 | −54 | 28.8 |
| 4 | Edenor OL-72 + Non. Acid[b] | 0.60 | 2.3 | 58 | −51 | — |
| 5 | Edenor OL-72 | 0.76 | 1.7 | 130 | −42 | 38.6 |
| 6 | Edenor OL-72 | 0.76 | 1.8 | 96 | −42 | 36.2 |
| 7 | Edenor OL-72 | 0.76 | 1.10 | 76 | −51 | 34.1 |
| 8 | Emery Ozone Acids + Nonanoic Acid | 0.50 | 1.25 | 236 | −30 | — |

[a]Esterified with TMP and nonanoic acid (where shown) and capped with nonanoic acid
[b]Non. Acid: nonanoic acid Table B shows further product characteristics for ester polyol esters produced using a two-step esterification process. The data shown supports the trend that ISO viscosities of ester polyol ester lubricant base oils increase with increasing values of DMR and decrease with increasing values of HCR of the corresponding ester polyols. Combination of these two trends predicts that a plot of DMR versus HCR for lubricant base oils having about the same ISO viscosity should be fairly linear since a predicted viscosity increase caused by increasing DMR should be mitigated or partially mitigated by a viscosity decrease predicted by increasing HCR.

Comparing Experiment 2 to Experiment 1 in Table B, similar ISO viscosities were obtained by simultaneously raising both the DMR and HCR values of simulated ozone acids. The product obtained from Experiment 3 versus Experiment 2 illustrates the increased ISO viscosity obtained when the polyol DMR is increased without increasing the HCR while Experiment 4 versus Experiment 3 illustrates the decreased ISO viscosity obtained when increasing HCR without increasing the DMR. Lubricant base oil candidates obtained in Experiments 5-7 did not incorporate any nonanoic acid so the DMR of the materials reflects the inherent DMR of ozone acids without modification. The polyols in Experiments 5-7 were generated under conditions generating maximum amounts of cross-linking and potential gel formation. As evidence that the compositions were close to the gel point, very small amounts of gel needed to be filtered to obtain clear solutions. However, the filtered solutions were well-behaved and again illustrate the inverse dependence of ISO viscosities on HCR values. The relatively high ISO viscosity lubricant base oil candidates have much lower pour points than typically observed in competing higher viscosity lubricant base oils.

Also shown in Table B is Experiment 8 where a relatively high viscosity material was obtained when using a moderately high DMR and low HCR to obtain an ISO viscosity of 236 cS. This material had a relatively low pour point of −30° C. and this property combined with its high viscosity could make this material a good candidate for a gear oil or grease base stock. The above results indicate that a range of increased ISO viscosity gear and grease base stock candidates may be produced by simultaneous increases in DMR and HCR values of ester polyols produced from the esterification of ozone acids with TMP.

As shown in Table B, lubricant base oil obtained by simultaneously increasing both DMR and HCR can have reduced materials cost while obtaining similar ISO viscosities. A major factor in generating reduced material costs is that increased amounts of relatively non-purified ozone acids are assumed to be lowest cost components are incorporated under these conditions. The reason for this effect is that increased DMR values are obtained by adding lower amounts of additional monoacids, such as, nonanoic acid to simulated ozone acid mixtures that results in increased ozone acid percentages. D illustrates this trend while providing DMR and HCR data for a series of lubricant base oil candidates produced from the above stated reactions.

From the above, it is similarly expected that the one-step esterification method of the present invention can be adjusted to produce products with a range of viscosities by changing the DMR of the reaction mixture.

Having now generally described the invention, the same will be more readily understood through reference to the following examples which are provided by way of illustration, and are not intended to be limiting of the present invention.

EXAMPLES

In the following examples, Azelaic acid mixtures and Pelargonic acid mixtures were supplied from Emery Oleochemicals (Malaysia) to formulate reaction mixtures.

Composition of Azelaic Acid:
 Azelaic acid (C9 diacid): min 72%
 Other diacid: 6-8%
 Monoacid: 13-15%

Composition of Pelargonic Acid:
 Pelargonic acid (C9 monoacid): 84-86%
 Other monoacid: 14-16%

Example 1 uses two esterification steps, the first step produces ester polyols using a molar excess of hydroxyl groups, and subsequently a second step that caps the remaining alcohol groups on the ester polyols by the use of a molar excess of monoacid, thereby producing ester polyol esters.

Examples 2-4 use a one-step process with a molar excess of carboxyl groups to directly produce ester polyol esters.

The different reaction formulations of Examples 2-4 result in products with a kinematic viscosity of 25, 44 and 100 cSt respectively.

In each reaction, a tin-based powder catalyst is used. Acid values after completion of the esterification for Examples 2-4 are below 20 mgKOH/g, and are below 1 mgKOH/g following purification (see purification procedure below). Hydroxyl Values after esterification & purification are below 5 mgKOH/g.

Each Example has a table showing product characteristics.

As shown herein, the use of a molar excess of carboxyl groups results in a reaction time that is commensurate to the two-step process, but is more economical to run. However, it has been found that using too much excess acid should be avoided as this can cause problems during purification of the ester polyol ester. In embodiments disclosed herein, it was found that a final targeted acid value of around 20 mgKOH/g works best in ensuring the reaction progresses speedily, while avoiding problems with purification. Further, a targeted acid value of 10 mg KOH/g had a stalling effect on the reaction, resulting in incomplete reaction and/or extended reaction times.

In the below experiments, it has also been found that the one-step method is significantly quickened by using excess acid in the reaction mixture. The average reaction time for Examples 2 to 4 is 7.5 to 8 hours, which is comparable to the total reaction time of 7.25 hours taken for both steps in the 2-step process, which would be needed for Example 1. This is in contrast to what was previously disclosed in U.S. 61/604,301, when a 1-step synthesis of ester polyol ester using an excess of alcohol groups took 12 hours compared to the total reaction time of 7.25 hours taken for both steps in the equivalent 2-step process.

While it is noted that Examples 2 to 4 were run on a laboratory scale (250 g to 350 g), it is expected that the same reaction time would be maintained using equipment capable of increasing the reaction temperature in line with the temperature ramp used on a laboratory scale.

Example 1

2-Step Process Using Tallow Based Ozone Acids

Lubricant 44 cSt
Step 1
Azelaic acid: 28.54 wt %
Pelargonic acid: 35.69 wt %
TMP: 35.77 wt %
Catalyst: 0.06 wt %
Step 2
Pelargonic acid: 46.8%
Catalyst: 0.06%

The reactants were mixed in the round bottom flask fitted with a gas inlet tube fitted with a gas dispersing block, a Vigareux distillation column fitted with a cooled condenser and collection flask to collect distilled water. The mixture was initially homogenized at 100° C. using mechanical stirring. The temperature was increased to activate the catalyst. The temperature was then increased to 180° C. and subsequently to 210° C. In order to drive the esterification to near completion, inert gas was sparged into the reaction mixture at a rate of 0.5 SCFH. The reaction was deemed complete when the acid value (AV) was less than 1 mg KOH/g. The ester polyols were then esterified or capped with pelargonic acid carboxylic acids to generate ester polyol esters.

Example 1 Result

| No | Description | Unit | Method | Polyol Ester LB25 |
|---|---|---|---|---|
| 1 | Appearance | — | Visual | B&C |
| 2 | Kinematic Viscosity, 40° C. | ° C. | ASTM D445 | 43.399 |
| 3 | Kinematic Viscosity, 100° C. | ° C. | ASTM D445 | 8.864 |
| 4 | Viscosity Index | — | ASTM D2270 | 154 |
| 5 | Colour | — | ASTM D1500 | L0 |
| 6 | Total Acid Number | mgKOH/g | ASTM D664 | 0.5 |
| 7 | Pour Point | ° C. | ASTM D97 | −54 |
| 8 | Flash Point | ° C. | ASTM D92 | >250 |

Example 2

1-Step Process Using Palm Based Ozone Acids

Lubricant 25 cSt
Azelaic acid: 2.69 wt %
Pelargonic acid: 75.87 wt %
Trimethylolpropane (TMP): 21.43 wt %
Catalyst: 0.03 wt %

The palm based ozone acids and polyhydric alcohol were mixed in the round bottom flask fitted with a gas inlet tube fitted with a gas dispersing block, a mechanical stirrer, a distillation column fitted with a cooled condenser and collection flask to collect distilled water. The mixture was initially homogenized at 100° C. using mechanical stirring. The temperature was increased to activate the catalyst. The temperature was then increased to 180° C. and subsequently to 210° C. In order to drive the esterification to near completion, inert gas was sparged into the reaction mixture at a rate of 0.5 SCFH. The reaction was deemed complete when the acid value (AV) was less than 20 mg KOH/g and hydroxyl value (HV) was less than 5 mg KOH/g.

Example 2 Result

| No | Description | Unit | Method | Polyol Ester LB25 |
|---|---|---|---|---|
| 1 | Appearance | — | Visual | B&C |
| 2 | Kinematic Viscosity, 40° C. | ° C. | ASTM D445 | 25.391 |
| 3 | Kinematic Viscosity, 100° C. | ° C. | ASTM D445 | 5.339 |
| 4 | Viscosity Index | — | ASTM D2270 | 150 |
| 5 | Colour | — | ASTM D1500 | L0 |
| 6 | Total Acid Number | mgKOH/g | ASTM D664 | 0.39 |
| 7 | Pour Point | ° C. | ASTM D97 | −54 |
| 8 | Flash Point | ° C. | ASTM D92 | 264 |
| 9 | Metal Analysis (Tin Content), ICP | Ppm | ASTM D4951 | 0 |
| 10 | 4 Ball | Mm | ASTM D4172 | 0.7 × 0.7 |

-continued

| No | Description | Unit | Method | Polyol Ester LB25 |
|----|---|---|---|---|
| 11 | Compositional Analysis, TGA | — | ASTM E1131 | 86.76% |
|    |  |  |  | 9.295% |
|    |  |  |  | 2.734& |
| 12 | Oxidative Stability, DSC | ° C. |  | 201.02 |
| 13 | Hydrolytic Stability |  | ASTM D2619 |  |
|    | TAN before hydrolytic stability | mgKOH/g |  | 0.58 |
|    | TAN after hydrolytic stability | mgKOH/g |  | 1.16 |
|    | Water acidity | mgKOH/g |  | 5.23 |
|    | Weight loss of copper strip | mg/cm2 |  | 0.11 |
|    | Appearance of the copper strip | cSt |  | 1B |
|    | Oil viscosity at 40° C. before hydrolytic stability | cSt |  | 25.30 |
|    | Oil viscosity at 40° C. after hydrolytic stability | % |  | 25.58 |
|    | Viscosity loss |  |  | 1.10 |
| 14 | Biodegradability | % | OECD 301B | 75.7 |

Example 3

1-Step Process Using Palm Based Ozone Acids

Lubricant 44 cSt
Azelaic acid: 9.64 wt %
Pelargonic acid: 67.86 wt %
Trimethylolpropane (TMP): 22.50 wt %
Catalyst: 0.03 wt %

The palm based ozone acids and polyhydric alcohol were mixed in the round bottom flask fitted with a gas inlet tube fitted with a gas dispersing block, a mechanical stirrer, a distillation column fitted with a cooled condenser and collection flask to collect distilled water. The mixture was initially homogenized at 100° C. using mechanical stirring. The temperature was increased to activate the catalyst. The temperature was then increased to 180° C. and subsequently to 210° C. In order to drive the esterification to near completion, inert gas was sparged into the reaction mixture at a rate of 0.5 SCFH. The reaction was deemed complete when the acid value (AV) was less than 20 mg KOH/g and hydroxyl value (HV) was less than 5 mg KOH/g.

Example 3 Result

Example 4

1-Step Process Using Palm Based Ozone Acids

Lubricant 100 cSt
Azelaic acid: 16.79 wt %
Pelargonic acid: 59.61 wt %
Trimethylolpropane (TMP): 23.6 wt %
Catalyst: 0.03 wt %

The palm based ozone acids and polyhydric alcohol were mixed in the round bottom flask fitted with a gas inlet tube fitted with a gas dispersing block, a mechanical stirrer, a distillation column fitted with a cooled condenser and collection flask to collect distilled water. The mixture was initially homogenized at 100° C. using mechanical stirring. The temperature was increased to activate the catalyst. The temperature was then increased to 180° C. and subsequently to 210° C. In order to drive the esterification to near completion, inert gas was sparged into the reaction mixture at a rate of 0.5 SCFH. The reaction was deemed complete when the acid value (AV) was less than 20 mg KOH/g and hydroxyl value (HV) was less than 5 mgKOH/g.

| No | Description | Unit | Method | Polyol Ester LB44 |
|----|---|---|---|---|
| 1 | Appearance | — | Visual | B&C |
| 2 | Kinematic Viscosity, 40° C. | ° C. | ASTM D445 | 46.329 |
| 3 | Kinematic Viscosity, 100° C. | ° C. | ASTM D445 | 8.356 |
| 4 | Viscosity Index | — | ASTM D2270 | 158 |
| 5 | Colour | — | ASTM D1500 | L0.5 |
| 6 | Total Acid Number | mgKOH/g | ASTM D664 | 0.68 |
| e | Pour Point | ° C. | ASTM D97 | −57 |
| 8 | Flash Point | ° C. | ASTM D92 | >250 |
| 9 | Metal Analysis (Tin Content), ICP | Ppm | ASTM D4951 | 0 |
| 10 | 4 Ball | Mm | ASTM D4172 | 0.7 × 0.7 |
| 11 | Compositional Analysis, TGA | — | ASTM E1131 | 60.52% |
|    |  |  |  | 29.27% |
|    |  |  |  | 7.856& |
| 12 | Oxidative Stability, DSC | ° C. |  | 201.61 |
| 13 | Hydrolytic Stability |  | ASTM D2619 |  |
|    | TAN before hydrolytic stability | mgKOH/g |  | 0.84 |
|    | TAN after hydrolytic stability | mgKOH/g |  | 1.76 |
|    | Water acidity | mgKOH/g |  | 12.99 |
|    | Weight loss of copper strip | mg/cm2 |  | 0.18 |
|    | Appearance of the copper strip | cSt |  | 1B |
|    | Oil viscosity at 40° C. before hydrolytic stability | cSt |  | 46.25 |
|    | Oil viscosity at 40° C. after hydrolytic stability | % |  | 46.87 |
|    | Viscosity loss |  |  | 1.34 |
| 14 | Biodegradability | % | OECD 301B | 83.6 |

Example 4 Result

| No | Description | Unit | Method | Polyol Ester LB100 |
|---|---|---|---|---|
| 1 | Appearance | — | Visual | B&C |
| 2 | Kinematic Viscosity, 40° C. | ° C. | ASTM D445 | 105.109 |
| 3 | Kinematic Viscosity, 100° C. | ° C. | ASTM D445 | 15.689 |
| 4 | Viscosity Index | — | ASTM D2270 | 159 |
| 5 | Colour | — | ASTM D1500 | L1.5 |
| 6 | Total Acid Number | mgKOH/g | ASTM D664 | 4.15 |
| 7 | Pour Point | ° C. | ASTM D97 | −48 |
| 8 | Flash Point | ° C. | ASTM D92 | >250 |
| 9 | Metal Analysis (Tin Content), ICP | ppm | ASTM D4951 | 0 |
| 10 | 4 Ball | mm | ASTM D4172 | 0.7 × 0.7 |
| 11 | Compositional Analysis, TGA | — | ASTM E1131 | 44.70% 44.39% 7.639% |
| 12 | Oxidative Stability, DSC | ° C. | | 200.61 |

TGA Thermogram Data

| Sample Name | Component 1 | Component 2 | Component 3 |
|---|---|---|---|
| Example 2 | 86.76% | 9.295% | 2.743% |
| Example 3 | 60.52% | 29.27% | 7.856% |
| Example 4 | 44.70% | 44.39% | 7.639% |

The above data show the major component distributions in Examples 2 to 4. In keeping with the polydispersity data, a single product predominates in Example 2, whereas Examples 3 and 4 show a differing distribution of ester polyol esters.

The following table compares estimated molar ratios based on reaction parameters for Examples 1-4. The estimated molar ratios are based on reaction formulations using 100% Azelaic acid and 100% Pelargonic acid, and not calculated from the exact composition used in the Examples. Reactant mass for each of Ex. 1 first step and Ex. 2-4 is assumed to be 100 g.

| | Ex. 1 first step^ | | | Ex. 2 | | | Ex. 3 | | | Ex. 4 | | |
|---|---|---|---|---|---|---|---|---|---|---|---|---|
| Compound (Mol. Wt) | % wt | # of mol | # of mol of functional groups | % wt | # of mol | # of mol of functional groups | % wt | # of mol | # of mol of functional groups | % wt | # of mol | # of mol of functional groups |
| Azelaic Acid (188.22) | 28.54 | 0.15163 | 0.30326 | 2.69 | 0.01429 | 0.02858 | 9.64 | 0.05122 | 0.10243 | 16.79 | 0.08920 | 0.17841 |
| Pelargonic Acid (158.23) | 35.69 | 0.22556 | 0.22556 | 75.87 | 0.47949 | 0.47949 | 67.86 | 0.42887 | 0.42887 | 59.61 | 0.37673 | 0.37673 |
| TMP (134.17) | 35.77 | 0.26660 | 0.79981 | 21.43 | 0.15972 | 0.47917 | 22.5 | 0.16770 | 0.50309 | 23.6 | 0.17590 | 0.52769 |
| Catalyst(N/A) | 0.06 | N/A | N/A | 0.03 | N/A | N/A | 0.03 | N/A | N/A | 0.03 | N/A | N/A |
| Excess Acid groups (mol) | | −0.27099 | | | 0.02891 | | | 0.02821 | | | 0.02745 | |
| Acid Value* (mgKOH/g) | | −177.6 | | | 17.8 | | | 17.4 | | | 17.0 | |
| HCR | | 1.51 | | | 0.94 | | | 0.95 | | | 0.95 | |
| DMR | | 0.67 | | | 0.029 | | | 0.12 | | | 0.24 | |

^Step 2: Add .476 mol pelargonic acid (46.8% wt = 75.3 g assuming first step results in product mass of 85.6 g), i.e. product of step 2 has 0.205 mol excess acid and an AV of 134.4
*Acid Value calculation takes into account water (Mw = 18.014) removed from reaction mixture Polydispersity Data Mn=number average molecular weight Mw=weight average molecular weight MP=peak molecular weight Mz=z average molecular weight Mz+1=z+1 average molecular weight Polydispersity=Mw/Mn

| Sample Name | Mn | Mw | MP | Mz | Mz + 1 | Polydispersity |
|---|---|---|---|---|---|---|
| Example 2 | 770 | 779 | 777 | 787 | 795 | 1.01 |
| Example 3 | 1032 | 1315 | 779 | 1788 | 2413 | 1.27 |

The above polydispersity data shows that the ester polyol esters produced in Example 2 differs very little in molecular weight, suggesting that a single ester polyol ester forms the majority of the product. In contrast, Example 3 contains a variety of different ester polyol esters. Without wishing to be bound by theory, this difference is caused by the increased amount of dicarboxylic acid present in Example 3, which allows for extended polymerisation to occur.

Removal of Free Fatty Acids and Catalyst

Instead of using standard steam distillation and deodorization methods for removing unreacted free fatty acids and catalyst, the unreacted acids and catalyst are removed via a combination of refining techniques. This combination of refining techniques has the flexibility to efficiently remove unreacted free fatty acid and catalyst present in the ester polyol esters and the process is outlined as follows.

1) Alkali or Basic Treatment
   a. Selection of alkali/basic treatment is determined by the free fatty acid content. In general, the minimum amount of the weakest strength necessary to achieve the targeted acid value, to minimize the saponification for the polyols and to prevent emulsions during separation.
   b. A de-emulsifier such as NaCl is added to reduce oil loss.
2) Mixing
   a. After the addition of the alkali/base solution, it must be adequately mixed to ensure sufficient contact with the oil in order the treatment is effective. Typically the alkali/base solution and oil are mixed at ambient temperature in a mixer with mild stirring with 3-5 minutes residence time.
   b. A high temperature during mixing must be avoided because it can increase the neutral oil saponification and reduce the refined oil yield. After the mixing is complete, the mixture is delivered to a centrifuge at a temperature suitable for optimum separation necessary to break the emulsion.

3) Soap-Oil Separation
   a. From the mixing phase, the resultant soap-in-oil suspension is fed to the centrifuge for separation into light and heavy density phases.
   b. Efficient separation of soapstock from the neutralized oil is the significant factor in alkali refining and the technique using centrifugal separators materially improves the yield.

4) Clay Refining
   a. Residual catalyst content can be removed using Montmorillonite clay adsorbent that is high in surface area providing excellent adsorption properties in attract metal oils.
   b. Both Montmorillonite and polyols will be heated at an optimum temperature for a specified time to ensure efficient adsorption of the catalyst.

In conclusion, selection of the alkali strength, mixing time, mixing energy, temperature, quantity of excess alkali, types and adsorbents all have an important part in making the refining process operate effectively and efficiently.

The above methodology was used to purify the ester polyol esters of Examples 1 to 4. However, steam distillation and deodorizing techniques can be used to effect the purification too.

The subject matter claimed herein is not limited to embodiments that solve any disadvantages or that operate only in environments such as those described above. Rather, this background is only provided to illustrate an exemplary technology area where some embodiments described herein may be practiced. Bibliographic references mentioned in the present specification are for convenience listed in the form of a list of references and added at the end of the examples. The whole content of such bibliographic references is herein incorporated by reference.

REFERENCES

1. WO 2010/078505
2. U.S. Pre-Grant Publication No. 2005/0112267
3. "The Preparation and Characterization of Trimethylolpropane Esters from Palm Kernel Oil Methyl Esters" (Robiah et al., *Journal of Oil Palm Research*, 15(2), December 2003, pp. 42-49)
4. Malaysian Patent No. 140833
5. U.S. Pat. No. 2,813,113
6. A. Spyros (J. Appl. Polym. Sci. 2002, 83, 1635).

The invention claimed is:

1. A method for preparing an ester polyol ester, the method comprising preparing a reaction mixture comprising:
   at least one polyol compound;
   at least one dicarboxylic acid; and
   at least one monocarboxylic acid,
   wherein the at least one polyol compound is esterified with the at least one dicarboxylic acid and the at least one monocarboxylic acid,
   wherein the reaction mixture has a hydroxyl group to carboxyl group ratio (HCR) corresponding to a ratio of moles of hydroxyl groups to moles of carboxyl groups, and the HCR is from 0.92 to 0.97, wherein
   the at least one polyol compound is trimethylolpropane;
   the at least one dicarboxylic acid is azelaic acid;
   the at least one monocarboxylic acid is nonanoic acid;
   the ester polyol ester produced by the esterification reaction has a kinematic viscosity at 40° C. of from 20 cSt to 110 cst; and
   the ester polyol ester has a pour point from −40° C. to −60° C..

2. The method according to claim 1, wherein the reaction mixture has the carboxyl groups in stoichiometric molar excess in comparison to the hydroxyl groups, wherein the molar excess of carboxyl groups in the reaction mixture provides an acid value (AV) of from about 11 mgKOH/g to about 40 mgKOH/g, optionally from about 12 mgKOH/g to about 30 mgKOH/g.

3. The method according to claim 1, wherein the reaction mixture has a difunctional/monofunctional Ratio (DMR) corresponding to a ratio of moles of dicarboxylic acid to moles of monocarboxylic acid and the compound has a viscosity proportional to the DMR of the reaction mixture, wherein the DMR is from about 0.03 to 0.5.

4. The method according to claim 3, wherein a lubricant base stock is formed from the ester polyol ester; the lubricant base stock having volatility inversely proportional to the Difunctional/Monofunctional Ratio (DMR) of the reaction mixture.

5. The method according to claim 1, wherein the method further comprises a catalyst, optionally wherein the catalyst is tin (II) oxide or tin(II)oxalate in a powder form in an amount from 0.01 wt % to 0.1 wt % of the reaction mixture.

6. The method according to claim 1, wherein the ester polyol ester produced by the esterification reaction is Formula III:

Formula III

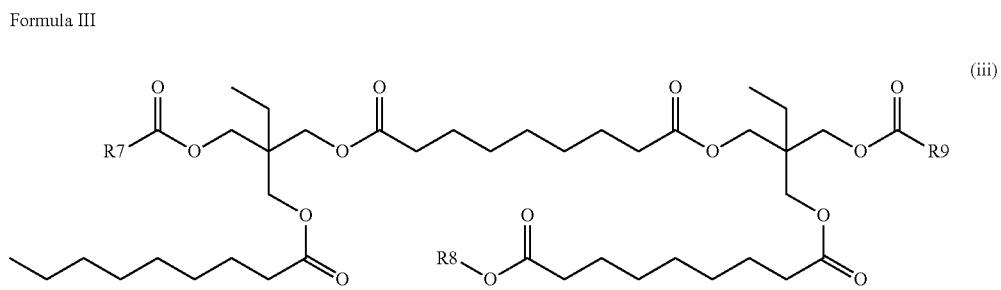

wherein R7, R8 and R9 are independently:
a linear or branched alkyl chain of between 1 to 17 carbon atoms, optionally substituted with one or more hydroxyl groups;
a C2-C18 linear alkyl chain with a terminal carboxylic acid group which is optionally esterified with a polyol compound of formula R10-OH; or
R10, wherein R10, when attached to a hydroxyl group, is a linear or branched primary polyol having from 2 to 12 carbon atoms and each alcohol functional group in R10 is optionally esterified with a linear or branched monocarboxylic acid having from 2 to 18 carbon atoms, or a dicarboxylic acid having from 2 to 18 carbon atoms.

7. The method according to claim 1, wherein:
(i) the at least one dicarboxylic acid further comprises at least one further dicarboxylic acid selected from oxalic acid, malonic acid, succinic acid, glutaric acid, adipic acid, pimelic acid, suberic acid, sebacic acid, 1,18-octadecanoic diacid and any combination thereof.

8. The method according to claim 1, wherein the method comprises:
(a) azelaic acid: 2.69 wt %; nonanoic acid: 75.87 wt %; and trimethylolpropane (TMP) 21.43 wt %;
(b) azelaic acid: 9.64 wt %; nonanoic acid: 67.86 wt %; and trimethylolpropane (TMP): 22.50 wt %; or
(c) azelaic acid: 16.79 wt %; nonanoic acid: 59.61 wt %; and trimethylolpropane (TMP): 23.6 wt %.

9. The method according to claim 3, wherein the DMR of the reaction mixture is from about 0.01 to about 0.5, optionally from about 0.015 to about 0.3.

10. The method according to claim 1, wherein the esterification reaction is considered complete when the reaction mixture has unreacted hydroxyl groups providing a hydroxyl value (HV) of less than about 10 mgKOH/g.

11. The method according to claim 1, wherein the at least one fatty acid is produced by hydrolyzing at least one triglyceride.

12. The method according to claim 1, wherein the ester polyol ester produced by the esterification reaction has a kinematic viscosity at 40° C. of from about 25 cSt ($10^{-6}$ $m^2 \cdot s^{-1}$) to about 105 cSt ($10^{-6}$ $m^2 \cdot s^{-1}$); and the ester polyol ester has a pour point from about −10° C. to about −70° C.

13. The method according to claim 1, wherein the method further comprises purification of the ester polyol ester, said purification comprising:
(a) contacting the crude reaction product with an aqueous solution containing an alkaline compound and a de-emulsifier to generate a mixture;
(b) subjecting the mixture to a mixing phase, comprising stirring the mixture for at least 3 minutes to form a soap-in-oil suspension, optionally the mixing phase is conducted at ambient temperature for up to 10 minutes;
(c) delivering the soap-in-oil suspension to a centrifuge at an optimum temperature to break soap-in-oil suspension, and collecting the ester polyol ester;
(d) subjecting the collected ester polyol ester to a Montmorillonite clay adsorbent treatment to remove any catalyst remaining in the collected ester polyol ester, optionally wherein the ester polyol ester and the clay are maintained at optimum temperatures; and
(e) collecting the purified ester polyol ester.

14. The method according to claim 13, wherein the molar excess of carboxyl groups in the reaction mixture following purification provides an acid value (AV) of less than about 1 mgKOH/g.

15. The method according to claim 6, wherein the ester polyol ester has the properties (a) to (e) listed under one of (i) to (iii):
(i):
(a) the HCR is about 0.94;
(b) the AV is about 18 mgKOH/g;
(c) the DMR is about 0.03;
(d) the at least one fatty acid is derived from palm fatty acids; and
(e) the ester polyol ester has a kinematic viscosity at 40° C. of about 25 cSt ($10^{-6}$ $m^2 \cdot s^{-1}$); or
(ii):
(a) the HCR is about 0.95;
(b) the AV is about 17 mgKOH/g;
(c) the DMR is about 0.12;
(d) the at least one fatty acid is derived from palm fatty acids; and
(e) the ester polyol ester has a kinematic viscosity at 40° C. of about 44 cSt ($10^{-6}$ $m^2 \cdot s^{-1}$); or
(iii):
(a) the HCR is about 0.95;
(b) the AV is about 17 mgKOH/g;
(c) the DMR is about 0.24;
(d) the at least one fatty acid is derived from palm fatty acids; and
(e) the ester polyol ester has a kinematic viscosity at 40° C. of about 105 cSt ($10^{-6}$ $m^2 \cdot s^{-1}$).

* * * * *